United States Patent [19]

Visconti et al.

[11] Patent Number: 4,545,903

[45] Date of Patent: Oct. 8, 1985

[54] APPARATUS FOR AUTOMATICALLY CONTROLLING THE SEDIMENTATION OF MUDS DURING THE PURIFICATION OF WASTE WATERS

[75] Inventors: Alfonso Visconti, Rome; Emilio Sernagiotto; Raffaello M. Sernagiotto, both of Voghera, all of Italy

[73] Assignee: Officine Meccaniche Sernagiotto, Pavia, Italy

[21] Appl. No.: 657,336

[22] Filed: Oct. 3, 1984

[30] Foreign Application Priority Data

Oct. 6, 1983 [IT] Italy .................... 23173 A/83

[51] Int. Cl.[4] ............................... C02C 1/26
[52] U.S. Cl. ........................... 210/96.1; 210/138; 210/143; 210/248
[58] Field of Search ............... 210/96.1, 94, 138, 143, 210/248

[56] References Cited

U.S. PATENT DOCUMENTS

| | | | |
|---|---|---|---|
| 2,122,922 | 7/1938 | Woods | 210/96.1 |
| 2,299,529 | 10/1942 | Crampton | 210/96.1 |
| 2,361,235 | 10/1944 | Pick | 210/96.1 |
| 3,812,966 | 5/1974 | Beach | 210/96.1 |
| 3,933,639 | 1/1976 | Pollastri et al. | 210/248 |
| 4,260,490 | 4/1981 | Moss et al. | 210/96.1 |

Primary Examiner—John Adee

[57] ABSTRACT

The apparatus for automatically controlling the sedimentation of muds during the purification of waste waters comprises a container for an amount of waste water of a material which is transparent to a signal responsive to the interface of the solid and liquid phases of said amount, transmitting and receiving means integral to one another respectively for transmitting and receiving said signal, forming a single unit and arranged at confronting position which is diametrically opposite to the axis of said container, means for relative movement between said container and unit controlled by the energization of said receiving means, position detecting means depending on time of said unit relative to said container, means for automatic loading and unloading of said container, and means for internal washing of the latter.

6 Claims, 3 Drawing Figures

APPARATUS FOR AUTOMATICALLY CONTROLLING THE SEDIMENTATION OF MUDS DURING THE PURIFICATION OF WASTE WATERS

The present invention is concerned with an apparatus for automatically controlling the sedimentation of muds during purification of waste waters.

In particular, the apparatus has been conceived for allowing the determination, automatically and at the desired time intervals, on different samples drawn at significant points of the purification plant of the following informations:

the mud condition;

the sedimentation curves of the mud (time, height, interface);

the derivates curves (time, velocity of interface lowering);

the initial settling velocity (ISV—m/h);

the Q limit (mc/h);

the mixed liquor suspended solids (M.L.S.S.);

the mud volume;

the mud concentration;

and other information which may be required for a correct operation of the plant.

As well known, purification plants comprise tanks of substantially impervious material, having stirrers for promoting the dissolution of atmospheric oxygen "$O_2$" in the waste water to be purified.

The oxygen thus dissolved enables the outliving of aerobic bacteria providing for phagocytying and biodegrading the polluting substances contained within the waste waters by the formation of muds separating by sedimentation from the liquid phase.

To this purpose, it is essential that the mud index (MI) given by the ratio of the sedimented mud volume and concentration of the suspended substances M L S S is within reduced values and anyhow about 120 ml/g.

At present, the control of these values is manually effected at regular intervals through the use of a conventional Imhoff cone.

It is the object of the present invention to provide a control apparatus for the sedimentation of muds in purification plants which operates continuously and completely automatically.

This and further objects of the invention will become apparent to those skilled in the art from the reading of the following description and claims.

The apparatus for automatically controlling the sedimentation of muds during the purification of waste water is characterized by providing a container for an amount of waste water under examination of transparent material to a signal which is responsive to the interface of the solid and liquid phases of said amount, transmitting and receiving means integral to one another respectively for transmitting and receiving said signal, forming a single unit and arranged at confronting position diametrically opposite to the axis of said container, means for relative movement between said container and said unit controlled by the energization of said receiving means, position detecting means depending on the time of said unit relative to said container, means for automatic loading and unloading of said container, and means for internal washing of the latter.

The invention is shown by only way of unrestrictive example in the figures of the single appended drawing sheet, in which.

Figure 1:
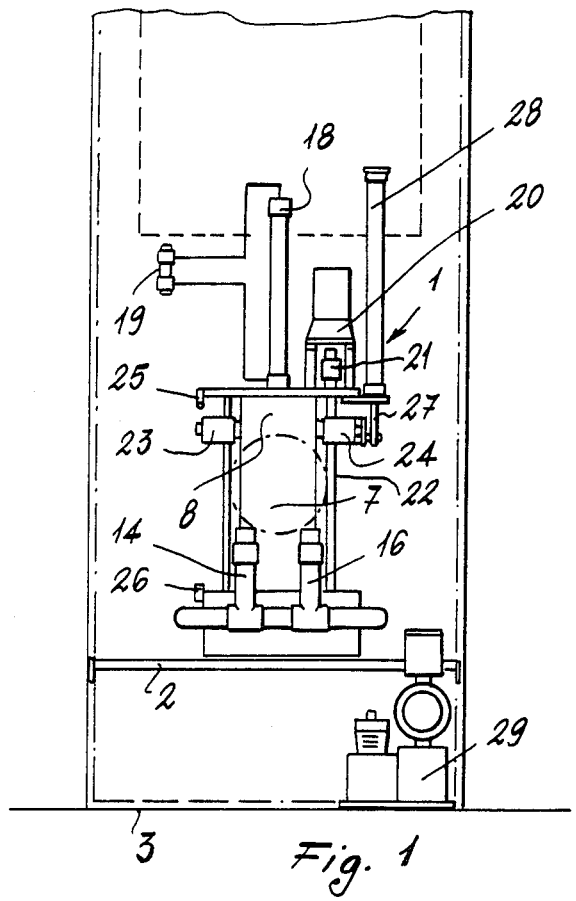
FIG. 1 is a front view of the apparatus.

Referring to the above figures of the accompanying drawing, an apparatus according to the invention, generally designated at 1, is fixed on supports 2 within a cabinet 3 provided with a pair of removable doors 4, a fixed door 5, a hinged door 6 and an inspection panel 7.

The apparatus 1 essentially comprises a closed container 8 of transparent material, connected to four conduits, that is a loading conduit 9, an overflow conduit 10, an unloading conduit 11, and a washing conduit 12, at the end of which and at the bottom of said container 8 a nozzle 13 is located for ejecting a conical spray.

Along said conduit 9 there are provided a pneumatic loading valve 14 and a washing shut off valve 15, while a pneumatic unloading valve 16 is provided along the washing conduit 12.

Figure 2:
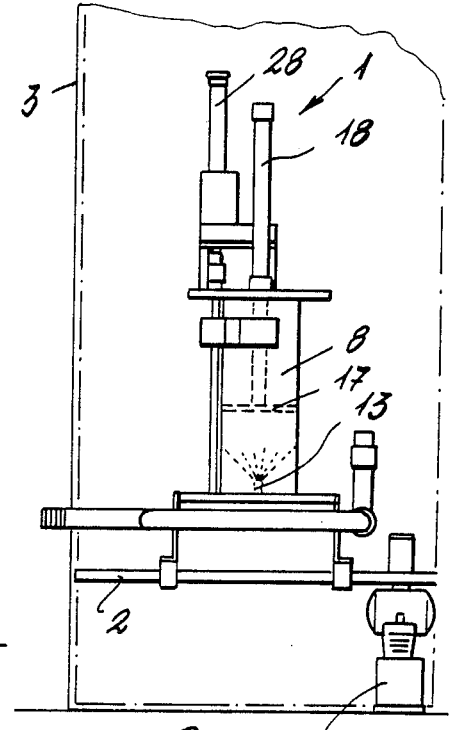
FIG. 2 is a side view.
Figure 3:
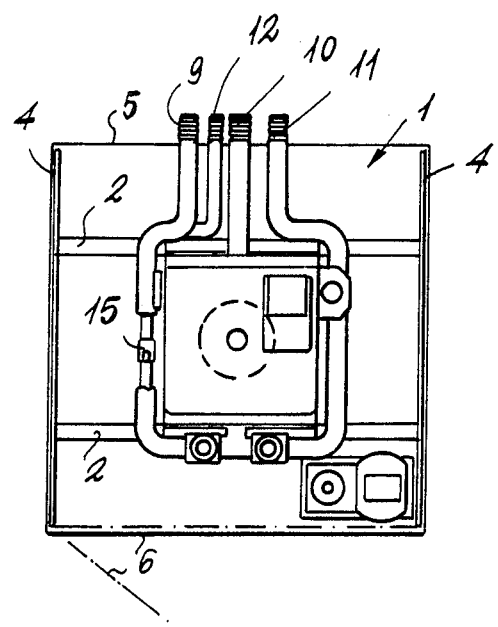
FIG. 3 is a top view of the apparatus.

Internally of the transparent container 8 there is provided an annular windscreen wiper 17 (shown by hatching in FIG. 2) driven by a pneumatic cylindr 18 which, in turn, is controlled by an electrovalve 19.

A motor 20 is integral with said container 8 and through an elastic or spring joint 21 operates a threaded bar 22 connected both to a transmitting photoelectric cell 23 and a receiving photoelectric cell 24, the latter being integral to each other, facing and arranged on opposite sides relative to the container 8.

A pair of end of strokes, upper end of stroke 25 and lower end of stroke 26, respectively, provide for defining the displacements of said photocells 23 and 24. The movable element 27 of a potentiometer 28 is directly connected to the photocells 23 and 24.

The apparatus is completed by an electrocompressor 29, intended for the operation of the pneumatic members of the apparatus and a pump, not shown, intended to overcome the head between the free surface of the waste waters in the tank and the position of the container 8.

The operation of the apparatus is as follows.

By means of the above mentioned pump, the waste waters being purified are drawn and introduced into the transparent container 8 through the loading conduit 9 until the overflow conduit 10 unloads the excess waste waters into the tank for a predetermined period of time; thus operating, the evacuation from the container 8 is allowed for the foulings being built up in the loading conduit 9 during the period of the pump inactivity and which the initial flow of the waste waters unavoidably draws along into the container 8.

Should these foulings not be evacuated by the overflow conduit 10, a systematic error in the sedimentation measurement would be caused.

At the end of the filling up operation, the pump is stopped and the sampling waste water under calm conditions will start to sediment or deposit increasingly sharply separating the liquid phase from the solid phase, enabling the receiving photocell 24 to pick up the signals of the transmitting photocell 23 supplied through the walls of the container 8 and liquid phase therein.

As striken by the signal, said photocell 24 will energize the motor 20 which, through the kinematic connection spring joint 21/threaded bar 22, will cause the photocell to move to a lower position until the receiving photocell 24 is de-energized, since the solid phase being desimented or deposited again conceals it. At the end of measurement, the photocells 23 and 24 will stop at the interface mud-liquid.

Similarly, also the moving element 25 will be displaced, causing a change in the electric values of the potentiometer 28. By suitably processing said electric values as a function of the apparatus constants and position attained by the photocells, the value of MI and liquid sedimentation speed can be obtained as a function of the programmed interval of time, it being as well possible to control and suitably automatically drive the equipment for the purification system.

At the end of measurement, the photocells move back to the initial or starting position, while the opening of valve 16 enables the examined waste water to be discharged through the conduit 11.

The valve 15 releases the passage of clean water in the washing conduit 12 and the nozzle 13 provides for washing the container 8, while the annular windscreen wiper 17, operated by the pneumatic cylinder 18, cleans the container walls.

The interruption of the water flow through the nozzle 13 and return of the annular windscreen wiper 17 to inactive or rest position presents the apparatus for the next cycle of observations.

It will be apparent to those skilled in the art that the above described apparatus can be used also for determining the sedimentation of substances other than those contained in waste waters, after a suitable adaptation of some members of the machine.

What we claim is:

1. An apparatus for automatically controlling the sedimentation of muds during purification of waste waters comprising:
   a container for containing an amount of waste water under examination, said container being in a material which is transparent to a signal responsive to the interface of the solid and liquid phases of said amount;
   transmitting and receiving means integral to one another respectively for transmitting and receiving said signal, said means forming a single unit arranged at confronting position diametrically opposite to the axis of said container;
   means for the relative movement between said container and said unit controlled by the energization of said receiving means;
   position sensing means as a time function of said unit relative to said container;
   means for the automatic loading and unloading of said container; and
   means for the internal washing of said container.

2. An apparatus as claimed in claim 1, wherein said transmitting and receiving means forming a single unit conveniently comprise a photocell system.

3. An apparatus as claimed in claim 1, wherein the means for relative movement between said container and said unit conveniently comprise a motor associated with a threaded bar with the interposition of a spring joint.

4. An apparatus as claimed in claim 1, wherein the position sensing means as a function of time conveniently comprise a potentiometer having its body integral with a fixed portion of the apparatus and the moving element integral with the moving portion of the apparatus.

5. An apparatus as claimed in claim 4, wherein the body of said potentiometer is integral with the container and the moving element is integral with said unit.

6. An apparatus as claimed in claim 1, wherein the container washing means comprises a nozzle located on the bottom of said container and sprinkling a water spray associated with an annular windscreen wiper provided with reciprocating motion and acting on the inner surface of the container.

* * * * *